United States Patent [19]

Hodges

[11] Patent Number: 4,947,152
[45] Date of Patent: Aug. 7, 1990

[54] PATIENT MONITORING SYSTEM

[75] Inventor: Harry A. Hodges, Escondido, Calif.

[73] Assignee: Mesa Vista Hospital, San Diego, Calif.

[21] Appl. No.: 827,894

[22] Filed: Feb. 10, 1986

[51] Int. Cl.$^5$ .............................................. G08B 25/00
[52] U.S. Cl. ................................ 340/573; 340/286.07; 340/600; 340/666
[58] Field of Search ............... 340/573, 575, 565, 600, 340/825.06, 825.19, 686, 666, 687, 556, 507, 286 R, 407, 286.07; 250/340

[56] References Cited

U.S. PATENT DOCUMENTS

| | | | |
|---|---|---|---|
| 3,668,682 | 6/1972 | Barbee et al. | 340/286 R |
| 4,175,263 | 11/1979 | Triplett et al. | 340/573 |
| 4,196,425 | 4/1980 | Williams, Jr. et al. | 340/573 |
| 4,225,852 | 9/1980 | Waters et al. | 340/286 R |
| 4,228,426 | 10/1980 | Roberts | 340/573 |
| 4,377,808 | 3/1983 | Kao | 340/600 |
| 4,510,488 | 4/1985 | St. Jean et al. | 340/600 |

Primary Examiner—Joseph A. Orsino, Jr.
Assistant Examiner—Brent A. Swarthout

[57] ABSTRACT

A patient monitoring system for altering a nurse if a hospital patient gets out of bed at night. The system has a detecting means such as an infrared motion detector for installation on a wall of a hospital room, an activating means responsive to an alert signal from the detecting means to activate a nurse call system, and a signal carrying means to carry the alert signal from the detecting means to the activating means. The signal carrying means comprises a radio transmitter disposed adjacent the detecting means to transmit the alert signal and a receiver to receive the transmitted signal and apply it to the activating means.

22 Claims, 1 Drawing Sheet

PATIENT MONITORING SYSTEM

BACKGROUND OF THE INVENTION

1. Field of the Invention

The present invention relates generally to systems for monitoring the activity of patients in hospital rooms.

2. The Prior Art

Hospital patients are susceptible to serious injury in slip-and-fall accidents. Elderly patients are especially vulnerable to such accidents while getting out of bed during the night or at other times when hospital personnel are not present. Most such accidents could be prevented if there were a way to alert a nurse as soon as a patient rises from bed so that the nurse could quickly go and assist the patient before the patient has had time to get out of bed and possibly fall.

Several kinds of hospital bed attachments have been devised to alert a nurse if a patient starts to get out of bed. For example, U.S. Pat. No. 4,228,426, issued to Roberts on Oct. 14, 1980, discloses patient monitoring apparatus comprising a switch installed in a pad positioned in bedding underneath the patient. If the patient gets up, the switch contacts open, generating an alarm signal. An electric cable connects the switch to a circuit external to the bed.

U.S. Pat. No. 4,196,425, issued to Williams, Jr., et al., on Apr. 1, 1980, discloses a photocell system wherein a plurality of optical energy emitters and photocells are installed in complementary locations on a hospital bed. If a patient in such a bed sits up or starts to get out of the bed, an energy beam is interrupted and an alarm signal is produced. As with the Roberts apparatus, a cable is required to carry electric power to the energy emitters and to carry the alarm signal from the bed to an external circuit.

Patient monitoring systems such as those disclosed by Roberts and Williams require that a sensing device, such as a switch in a pad, a photocell and optical energy source, or the like, be installed in the bed and that a cable be used to connect said sensing device to an external circuit. This cable poses a hazard in that the patient may trip on the cable while getting out of bed. Also, the presence of an electrically powered device in the bed presents a risk of electric shock. In addition, electrical devices and cables in the bed interfere with making up the bed or moving it for cleaning purposes and often annoy the patient.

It will be apparent from the foregoing that there is a need for a patient monitoring system located remote from the bed and adapted to alert a nurse if a patient gets out of bed. The present invention satisfies this need.

SUMMARY OF THE INVENTION

The present invention provides a patient monitoring system that alerts a nurse when a patient gets out of bed but that has no components mounted in or on the bed itself.

A patient monitoring system according to the present invention comprises a detecting means that generates an alert signal in response to presence of a patient in a predetermined zone spaced apart from the bed; activating means to activate a nurse call system in response to the alert signal; and signal carrying means such as a radio transmitter and receiver to carry the alert signal from the detecting means to the activating means In a preferred embodiment, the detecting means comprises an infrared motion detector mounted on a wall. The detector responds to the presence of a patient within a fanshaped zone that extends from the detector across the patient's room and that is necessarily occupied by a person standing near the bed. This zone is above and spaced apart from the bed so that the detector does not respond to normal movement of a patient sleeping in the bed.

The activating means may comprise a latching relay having a normally-open contact connected in parallel with a nurse call button. Once the relay has been energized, it remains energized until manually reset, thereby insuring that the nurse call signal will not cease until a nurse arrives at the patient's bedside and manually resets the relay.

The transmitter and the motion detector can be battery powered and mounted next to each other in any convenient, unobtrusive location remote from the bed and without any need for power cables or other connecting wires. The receiver is installed near the activating means.

In an alternate embodiment, a cable serves in place of the transmitter and receiver as the signal carrying means. The cable can be routed from the detecting means to the activating means in an unobtrusive place such as along a baseboard molding.

It will be appreciated from the foregoing that the present invention represents a significant advance in patient monitoring systems in that, although no part of the system is mounted in or on the bed, a nurse call system is activated as soon as the patient rises from the bed. Other aspects and advantages of the present invention will become apparent from the following more detailed description taken in conjunction with the accompanying drawings.

DESCRIPTION OF THE PREFERRED EMBODIMENT

Existing patient monitoring systems require the installation of potentially hazardous electrical apparatus and cables in a hospital bed. The present invention provides a patient monitoring system that has no components in the bed but that alerts a nurse as soon as a patient rises from the bed.

Figure 1:
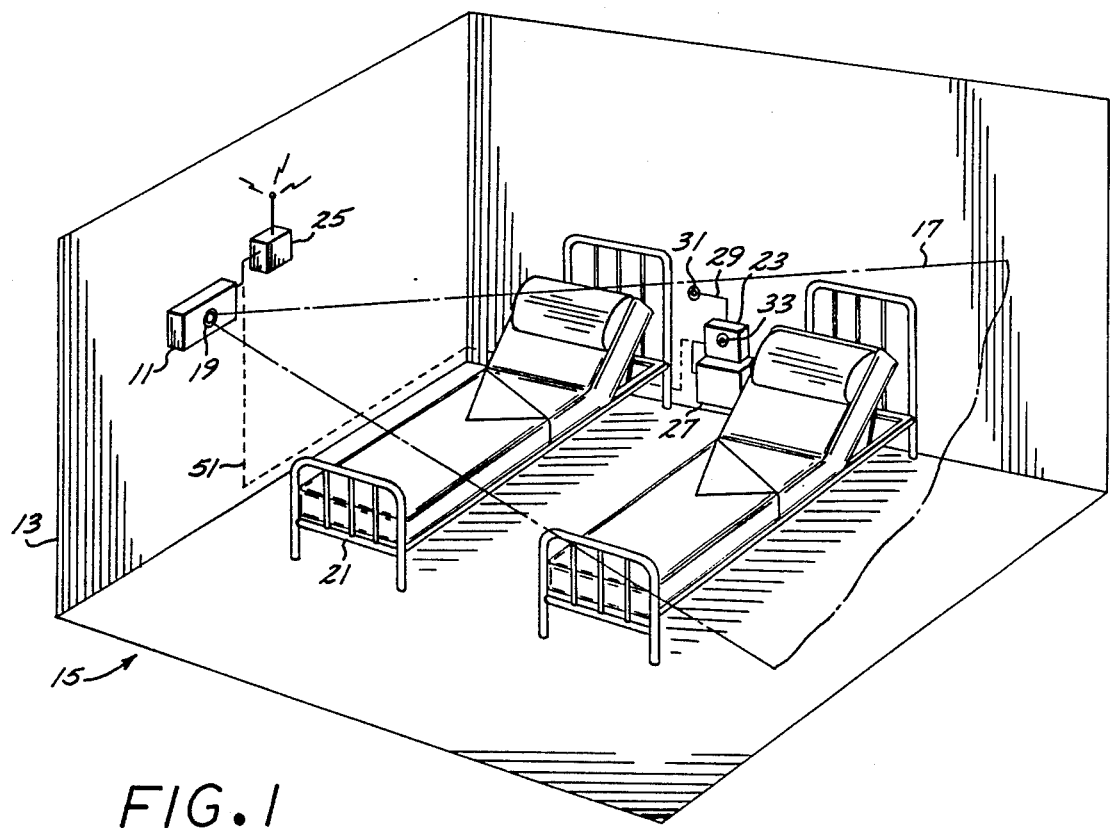
FIG. 1 is a perspective view of a patient monitoring system according to the present invention.

In accordance with the invention, a detecting means 11 is mounted on a wall 13 of a hospital room 15, as shown in FIG. 1. The detecting means 11 may be any device operative to generate an alert signal in response to the presence of a patient within a predetermined fan-shaped zone 17 that extends from a sensing element 19 of the detecting means 11 across a hospital bed 21. One suitable and readily available detecting means comprises a passive infrared motion detector that responds to a change in infrared energy emissions within the zone 17.

The zone 17 is spaced far enough above the bed 21 to prevent the detecting means 11 from responding to normal motion of a sleeping patient in the bed 21, but low enough to enable the detecting means 11 to respond to a standing patient and, if desired, to a patient sitting up in bed.

The alert signal is carried to a nurse call activating means 23 by a signal carrying means comprising, for example, a radio transmitter 25 that transmits the alert signal and a receiver 27 that receives the transmitted alert signal.

Figure 2:
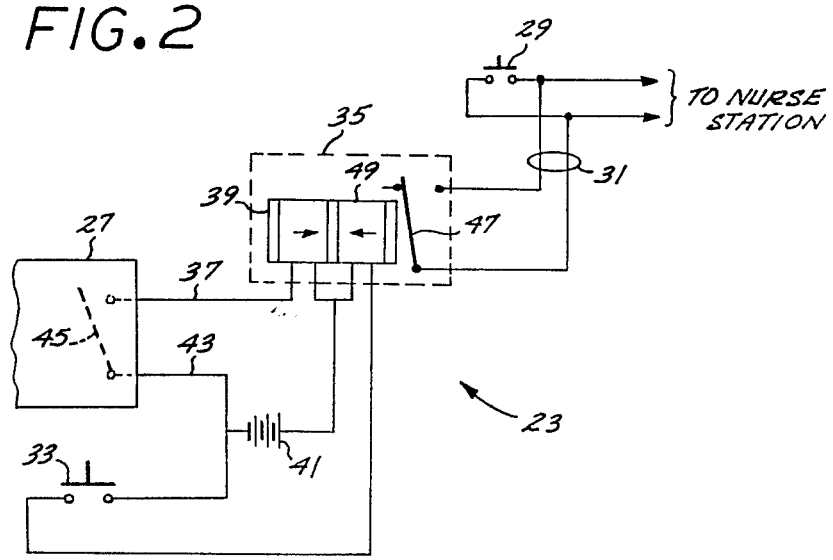
FIG. 2 is a schematic of an activating means forming a part of the patient monitoring system of FIG. 1.

Upon receipt of the alert signal, the activating means 23 activates a nurse call circuit through a cable 29. The nurse call circuit may comprise, for example, a normally-open nurse call button 31. A reset button 33 is used by a responding nurse to reset the activating means 23. More particularly, as best seen in FIG. 2, the activating means 23 comprises a latch circuit, such as a latching relay 35. It will be apparent that a solid state latch circuit having a device such as an SCR or a flip-flop could be used in place of the latching relay 35.

An electrical conductor 37 couples the receiver 27 to a first terminal of a latch coil 39 of the relay 35. A second terminal of the latch coil 39 is electrically connected to a first terminal of an electrical power source 41, which may be a battery or the like. A second terminal of the power source 41 is connected by an electrical conductor 43 to the receiver 27.

The receiver 27 is operative to couple the conductors 37 and 43 through a switch contact 45 or the like upon receipt of an alert signal from the transmitter 25, applying power to the latch coil 39 and thereby causing a normally open relay contact 47 to latch closed. The relay contact 47 is connected in parallel with the nurse call button 31 through the cable 29, and when the relay contact 47 is latched closed a warning signal is produced at a nurse station by well-known apparatus not forming a part of the present invention.

A nurse entering the room 15 in response to the warning signal can terminate the warning signal by pressing the reset button 33. The button 33 has a first terminal connected to a first terminal of an unlatch coil 49 of the relay 35. A second terminal of the unlatch coil 49 is connected to the first terminal of the power source 41. The second terminal of the power source 41 is connected to a second terminal of the button 33. When the button 33 is pressed, the unlatch coil 49 is activated, opening the relay contact 47 and thereby terminating the warning signal at the nurse station.

The transmitter 25 and the detecting means 11 are battery powered and therefore may be placed at any suitable location in the room 15 without the need of any power or other cable connection. If desired, the transmitter and the detecting means can be incorporated into a single unit; such a unit is available under the designation "Aztec model 1699 Wireless Passive Infrared Motion Detector," distributed by Ademco of New York, NY.

In an alternate embodiment, the transmitter 25 and the receiver 27 are replaced by a cable 51. The cable 51 carries the alert signal from the detecting means 11 directly to the activating means 23. The cable 51 is preferably installed out of the way, such as along a baseboard molding. It need not be attached to the bed 21.

The zone 17 preferably extends across the entire room 15. Consequently, if there are one or more other beds in the room 15, the detecting means 11 generates an alert signal in response to a patient getting out of any of the beds.

In summary, a patient monitoring system according to the present invention activates a nurse call system as soon as a patient arises from a hospital bed so that a nurse can quickly come and assist the patient before the patient gets into a position to trip and fall. The system has no parts located on or in the bed and accordingly poses no hazard to the patient and is not in the way of the patient or anyone who must make up or move the bed.

Various modifications and changes may be made with regard to the foregoing detailed description without departing from the spirit of the invention. It is therefore to be understood that, within the scope of the appended claims, the invention may be practiced otherwise than as specifically described.

I claim:

1. A patient monitoring system for automatically activating a nurse call system, comprising:
   passive energy detecting means including a sensing element adapted for location on a wall in a hospital room remotely of any bed in the room whereby such bed may be moved independently of the sensing element, operative to generate an alert signal in response to a change in ambient energy resulting from intrusion by a patient into an alarm zone spaced above any bed in the room and extending from the sensing element generally horizontally across the room in a fan-shaped pattern of sufficient breadth that a bed located at substantially any point in the room is at least partially under the zone;
   nurse call activating means responsive to the alert signal to activate the nurse call system; and
   signal carrying means to carry the alert signal from the detecting means to the nurse call activating means.

2. A system according to claim 1 wherein the detecting means is battery powered.

3. A system according to claim 1 wherein the detecting means comprises an infrared motion detector operative to sense infrared radiation present in said zone and responsive to a change in said radiation to generate the alert signal.

4. A system according to claim 1 wherein the detecting means is unresponsive to presence of the patient outside said zone whereby the alert signal is not generated by movement of a reclining patient outside said zone within any bed in the room.

5. A system according to claim 1 wherein the activating means comprises a latching circuit having a latching switch element in electrical communication with a nurse call button circuit in the room and responsive to the alert signal to latch and thereby continuously activate the nurse call system through said nurse call button circuit.

6. A system according to claim 5 and further comprising manual reset means operative to unlatch the latch circuit and thereby discontinue the activation of the nurse call system.

7. A patient monitoring system for automatically activating a nurse call system, comprising:
   passive energy detecting means including a sensing element adapted for location on a wall in a hospital room remotely of any bed in the room whereby such bed may be moved independently of the sensing element, operative to generate an alert signal in response to a change in ambient energy resulting from intrusion by a patient into an alarm zone spaced above any bed in the room and extending from the sensing element generally horizontally across the room in a fan-shaped pattern of sufficient breadth that a bed located at substantially any point in the room is at least partially under the zone;

a transmitter responsive to the detecting means to transmit the alert signal when presence of the patient within said zone is detected;

a receiver to receive the alert signal from the transmitter; and nurse call activating means responsive to the receiver to activate the nurse call system when the alert signal is received.

8. A system according to claim 7 wherein the transmitter and the detecting means are battery powered.

9. A system according to claim 7 wherein the detecting means comprises an infrared motion detector operative to sense infrared radiation present in said zone and responsive to a change in said radiation to generate the alert signal.

10. A system according to claim 7 wherein the detecting means is unresponsive to presence of the patient outside said zone whereby the alert signal is not generated by movement of a reclining patient outside said zone within any bed in the room.

11. A system according to claim 7 wherein the activating means comprises a latching circuit having a latching switch element in electrical communication with a nurse call button circuit in the room and responsive to the alert signal to latch and thereby continuously activate the nurse call system through said nurse call button circuit.

12. A system according to claim 11 and further comprising manual reset means operative to unlatch the latch circuit and thereby discontinue the activation of the nurse call system.

13. A system according to claim 5 wherein the latching switch element comprises a normally-open switch contact and wherein the electrical communication between said element and the nurse call button circuit is established by a connection of said contact across said circuit in parallel with any nurse call button also connected to said circuit.

14. A system according to claim 11 wherein the latching switch element comprises a normally-open switch contact and wherein the electrical communication between said element and the nurse call button circuit is established by a connection of said contact across said circuit in parallel with any nurse call button also connected to said circuit.

15. In a patient care facility room having walls and one or more beds, a patient monitoring system for activating nurse call activating means when a patient in one of the beds intrudes into an alarm zone having a generally horizontally oriented lower boundary extending substantially throughout the room and located sufficiently above the bed that normal movements of a reclining patient do not intrude the patient into the alarm zone, the system comprising:

passive energy detecting means including a sensing element located on one of the room walls remotely of the bed whereby the bed may be moved independently of the sensing element, the detecting means being inoperative in response to movements of a reclining patient in the bed but operative to generate an alert signal in response to raising up of the patient and intrusion into the alarm zone;

nurse call activating means responsive to the alert signal to activate the nurse call system; and signal carrying means to carry the alert signal from the detecting means to the nurse call activating means.

16. A system according to claim 15 wherein the detecting means is battery powered.

17. A system according to claim 16 wherein the signal carrying means comprises a battery-powered radio transmitter responsive to the detecting means to transmit the alert signal and a receiver to receive the alert signal from the transmitter.

18. A system according to claim 15 wherein the detecting means comprises an infrared motion detector operative to sense infrared radiation present in said zone and responsive to a change in said radiation to generate the alert signal.

19. A system according to claim 15 wherein the detecting means is unresponsive to presence of a patient outside said zone whereby the alert signal is not generated by movement of a reclining patient outside said zone within any bed in the room.

20. A system according to claim 15 wherein the activating means comprises a latching circuit having a latching switch element in electrical communication with a nurse call button circuit in the room and responsive to the alert signal to latch and thereby continuously activate the nurse call system through said nurse call button circuit.

21. A system according to claim 20 wherein the latching switch element comprises a normally-open switch contact and wherein the electrical communication between said element and the nurse call button circuit is established by a connection of said contact across said circuit in parallel with any nurse call button also connected to said circuit.

22. A system according to claim 20 and further comprising manual reset means operative to unlatch the latch circuit and thereby discontinue the activation of the nurse call system.

* * * * *